United States Patent [19]

Teitelbaum et al.

[11] Patent Number: 4,572,179
[45] Date of Patent: Feb. 25, 1986

[54] APPARATUS FOR REMOVING SWINE TAILS

[76] Inventors: Jay M. Teitelbaum; Henry S. Teitelbaum, both of 3840 S. Jason St., Engelwood, Colo. 80110

[21] Appl. No.: 294,939

[22] Filed: Aug. 21, 1981

[51] Int. Cl.4 ............................................. A61B 17/00
[52] U.S. Cl. .................................. 128/303 A; 29/235
[58] Field of Search .................... 29/235, 235.5, 268; 81/306–309, 303, 383.5, 349, 310–312; 128/321, 345, 303 A; 433/154, 159

[56] References Cited

U.S. PATENT DOCUMENTS

| | | | |
|---|---|---|---|
| 1,250,690 | 12/1917 | Stallings | 81/309 |
| 2,582,640 | 1/1952 | Maddox | 128/303 A |
| 2,840,081 | 6/1958 | Moose | 128/303 A |
| 2,840,082 | 6/1958 | Salvatore | 128/303 A |

FOREIGN PATENT DOCUMENTS 666798 10/1938 Fed. Rep. of Germany ... 128/303 A

Primary Examiner—Michael H. Thaler
Attorney, Agent, or Firm—Herbert C. Schulze

[57] ABSTRACT

This invention is a method, and an apparatus for practicing said method, wherein a resilient ring-like member of rubber or the like is expanded in a triangular configuration and slipped over the tails of swine for the purposes of totally interrupting the flow of blood and causing the tail to drop off, at the same time requiring no surgery or other techniques causing a loss of blood. The method utilizes a particular apparatus, a unique invention in itself, for expanding the ring in an unusual, economical, and rapid manner. The expanding apparatus comprises a pair of pegs mounted on jaws and activated away from one another by a pair of handles which in turn activate a third peg cooperating with the first two to form a triangular configuration.

1 Claim, 13 Drawing Figures

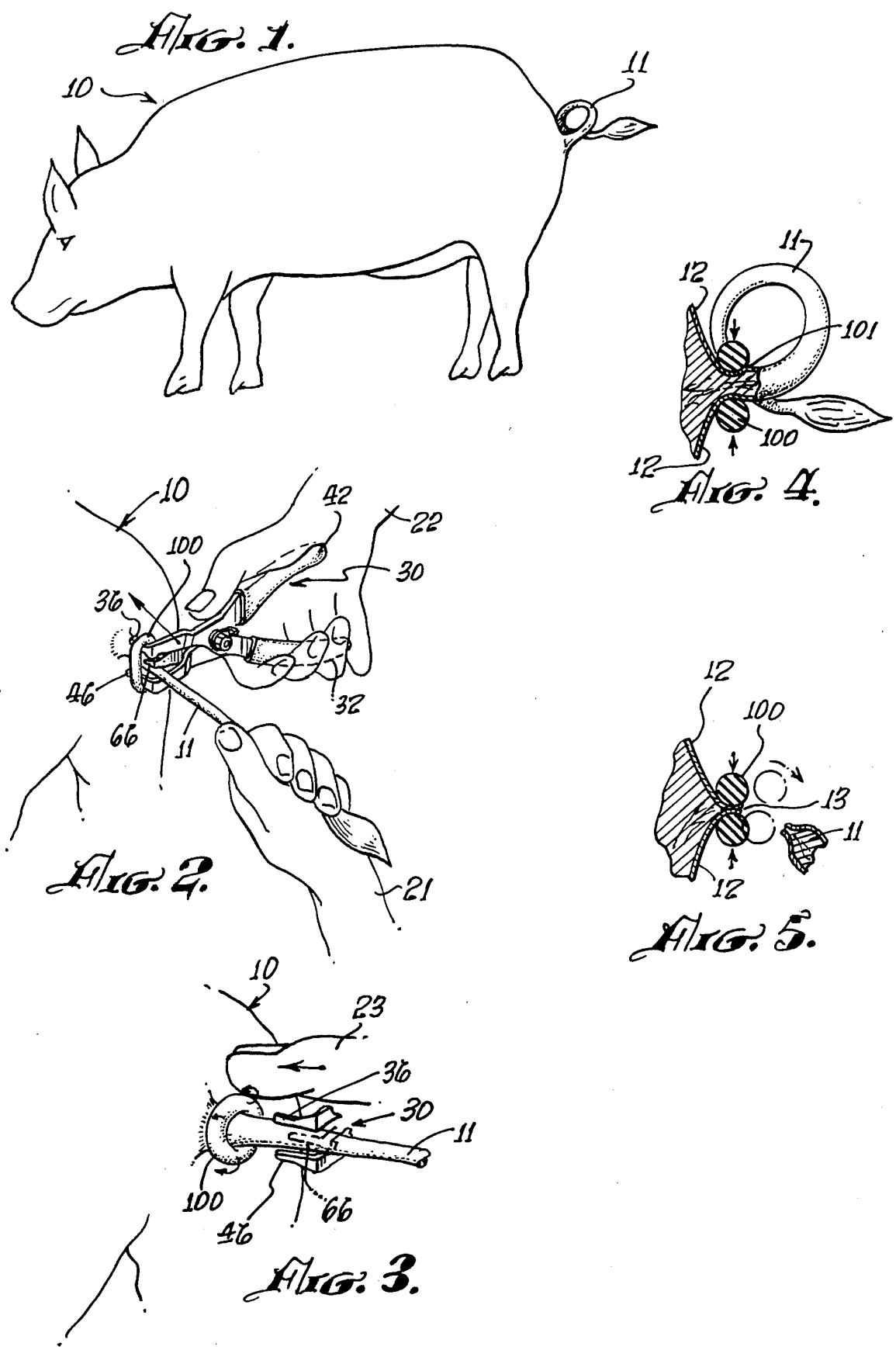

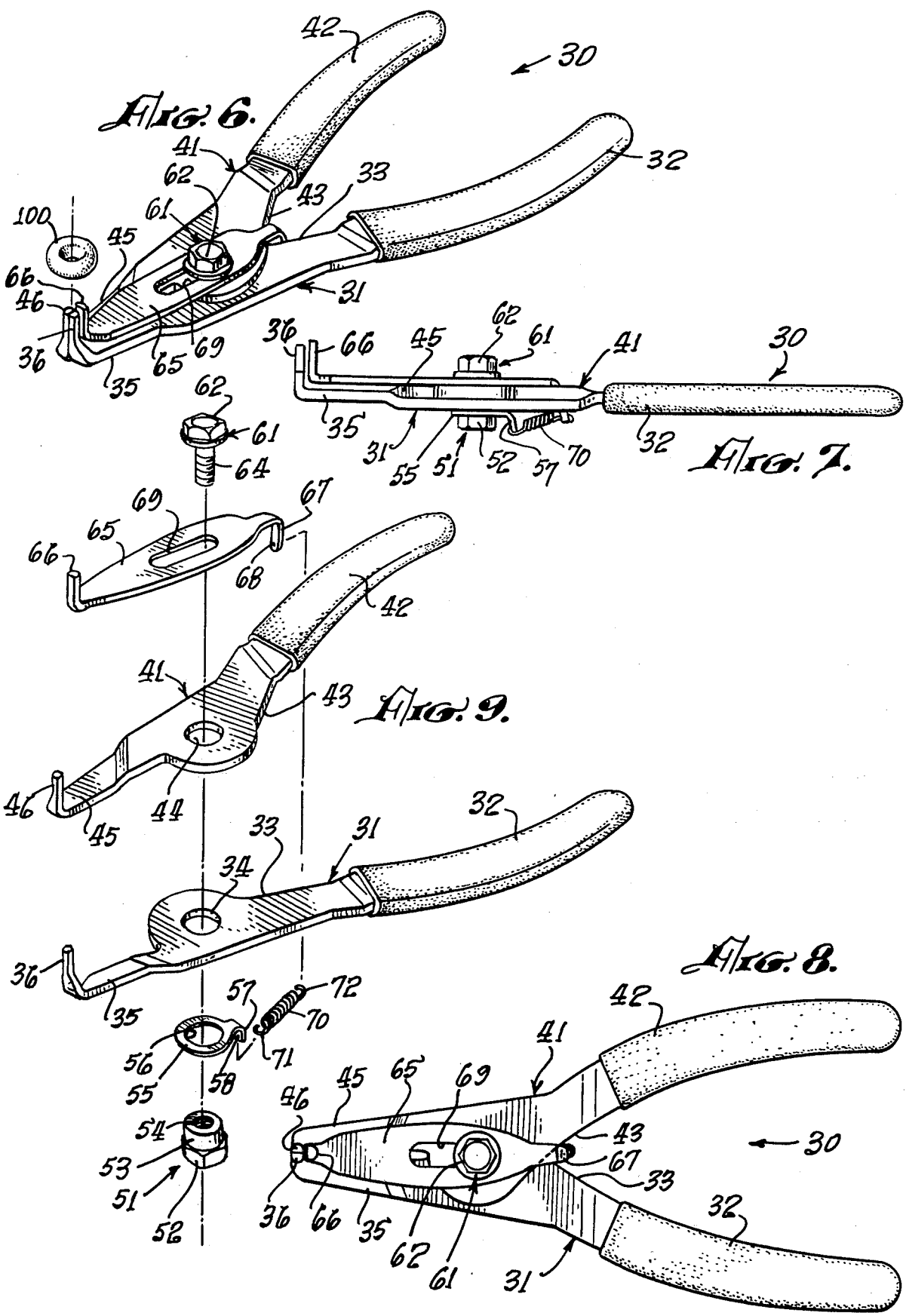

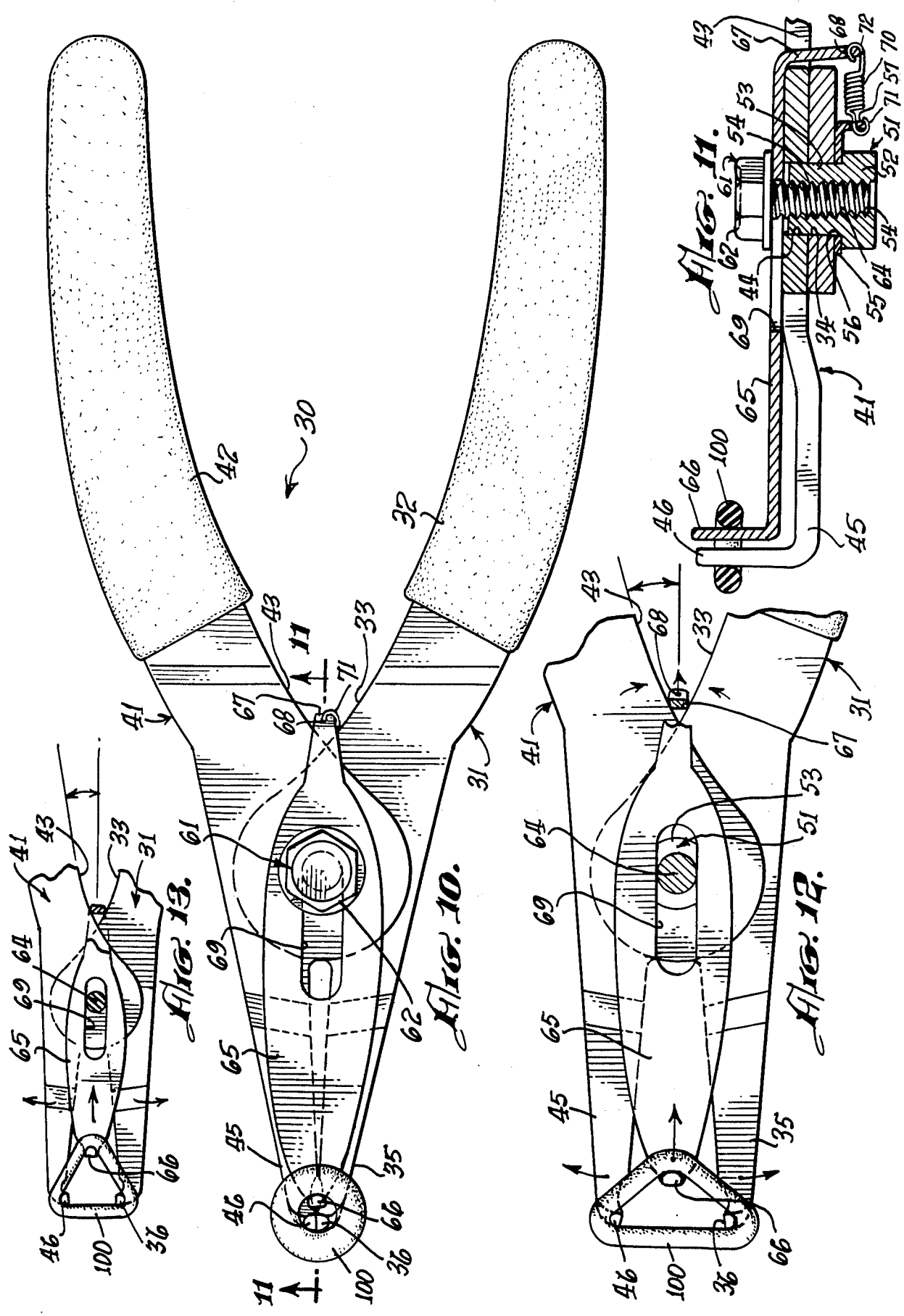

APPARATUS FOR REMOVING SWINE TAILS

CROSS REFERENCE TO RELATED PATENT APPLICATIONS

There are no patent applications filed by us related to this application, with the exception of design patent application on "Expander Tool" being filed by us concurrent with this application.

BACKGROUND OF THE INVENTION

1. Field of the Invention

This invention is in the general field of methods and apparatus for non-surgical removal of animal tails, horns, testicles, and the like. It is further directed to the foregoing mentioned field wherein a resilient ring of rubber, or the like, is formed, having is very small opening but being expandable to slip over the portion of the animal to be non-surgically removed and then released onto such member so as to completely cut-off the flow of blood from the main portion of the animal to the member, at the same time pulling the skin adjacent the animal into a configuration such that the skin covers the area from which the member was removed. The invention is even further directed to the non-surgical removal of tails from swine by expanding the ring in a unique triangular configuration by utilization of a unique ring expanding tool and applying the ring around the tail of the swine and removing the ring from the expanding tool.

2. Description of the Prior Art

It has been known for a long time that it is possible to non-surgically remove tails from dogs, horns from calves, testicles from various animals, and the like, by totally shutting off the circulation of blood from the animal to the appendage being, or to be, removed. The well known Minock products manufactured in Denver, Colo. are exemplary of the type of ring (normally latex) used for this purpose. There have been various devices constructed for expanding the latex rings. All of such devices utilize a number of protrusions about an expandable mechanism. The ring is placed over the protrusions, expanded so as to be able to be slipped over the animal appendage being removed, and then released onto the appendage. All of such expanders utilize a plurality of ring expanding protrusions ranging from four or more in number. Such expanders are costly and cumbersome. Additionally, they do not form an elongated opening suitable to accommodate a thin appendage having a substantial width.

All of the expanders heretofore known further have the difficulty that with a number of protrusions it is not possible to effectively place a rubber ring with an extremely small hole upon the large number of protrusions. Further, it is frequently difficult to remove the ring from the apparatus of the prior art, especially with the use of one hand.

The present invention is unique in that it provides for the expansion of a ring with a very small inner diameter which can be slipped over the tails of swine for purpose of removing the tail, and especially the expander used in the method of this invention now, for the first time, utilizes three members only for the purpose of insertion within the ring and provides a triangular opening which is particularly adaptable to use in connection with some odd configurations frequently encountered in the animal members, particularly the tails of swine, being removed. The method and the apparatus of this particular invention become a unique and valuable advance in this art and make certain procedures heretofore impossible, possible. In this respect, it is unique and without prior art.

SUMMARY OF THE INVENTION

We have been engaged in study and experimentation with the removal of animal members such as calves' horns, dogs' tails, animals' testicles, and the like, for a great period of time.

It is frequently desirable to castrate animals such as steer and the like as is known to those familiar with animals and their characteristics. It is also frequently desirable to de-horn calves and the like.

For purposes of those involved with dogs, it is frequently desired to dock the dogs' tails, and essential to do so for many show purposes. This has been usually accomplished either by surgery or by the use of a latex ring as has heretofore been mentioned slipped over the dog's tail for the purpose of completely interrupting circulation so that in due course the tail will actually literally drop off and there will not be pain to te animal nor a loss of blood or unsightly surgical scars. The same principle takes place when latex rings or the like are used for de-horning, castration, or other such purposes.

Customarily the latex rings used have a relatively small hole in the center and have sufficient elastic strength such that when placed over the member to be removed the entire blood circulation is interrupted. Further, the rings are customarily of such thickness of material as to cause a gradual pulling action about the skin adjacent the main animal body so that when the member finally drops off as a result of the total interruption of blood flow, the skin has been rolled or pulled in such fashion that there is no unsightly scar and at the most a very slight callous at the tip of the position from which the was removed.

The method by which this is accomplished is to expand the ring by placing it over a number of closely configured ring expanding and holding members which are connected to complex mechanisms which cause them to spread from one another until the center of the ring is large enough to be slipped over the member to be removed. At this time the ring is then pushed off of the end of the protrusions and tightens itself about the member at the place desired. Such mechanisms requiring a number of protrusions cause a limit to the size of the hole. Also the mechanisms are bulky, expensive and sometimes difficult to handle.

A particularly interesting field of the removal of tails from animals is in the swine industry. When in feeding lots where a number of swine are confined to a pen with other swine in adjacent pens, the swine have a tendency to bite the tails of swine in adjacent pens if they slip through the bars or other barrier between the pens. This creates a serious problem since there is a large artery in the tail of the swine and a great deal of bleeding occurs.

For the foregoing reason, it has become increasingly popular to surgically dock, or remove, the tails from swine. It has been difficult, if not impossible, to utilize the latex ring method heretofore discussed for removing the tail from swine because of the frequently odd configuration of the tail and its thin nature.

We have studied this at length and have now solved this problem and have perfected a method, and an apparatus for practicing the method, wherein three pegs are inserted within the opening of a latex ring having a very small hole and by a simple lever action the three pegs are caused to move outwards so as to expand the ring appropriately to slip over the swine's tail.

In accomplishing this, we have utilized a pair of pegs mounted on jaws and pivotally connected to a pair of handles such that when the handles are squeezed together the pegs spread apart. We have added a third peg which is mounted upon a sliding action mechanism between the interior portions of the handles of the two jaws such that it is automatically pulled away from the first two pegs as they spread apart. Thus, a ring placed upon these three protrusions is caused to open in a triangular configuration. This has not heretofore been accomplished by any of the devices available.

It is an object of this invention to provide a method for placing latex rings or the like over the tails of swine for purpose of removing the tails.

Another object of this invention is to provide an apparatus to perform the aforesaid method.

Another object of this invention is to provide a method and apparatus for deforming latex rings or the like into a triangular configuration.

The foregoing and other objects and advantages of this invention will become apparent to those skilled in the art upon reading the description of a preferred embodiment which follows in conjunction with a review of the appended drawings.

BRIEF DESCRIPTION OF THE DRAWINGS

FIG. 1 is a schematic perspective of a pig showing particularly the customary tail configuration;

FIG. 2 is a schematic perspective of the tail being slipped through a ring expanded by the apparatus of this invention;

FIG. 3 is a schematic perspective of a portion of the tail showing how the ring is placed in its working position upon the tail;

FIG. 4 is a partially sectioned schematic perspective showing the action of the ring upon the tail of the pig;

FIG. 5 is a schematic partially sectioned view illustrating the manner in which the tail is finally removed and the skin is caused to adhere over the remaining stub;

FIG. 6 is a perspective of a preferred embodiment of an apparatus to practice the method of this invention;

FIG. 7 is a side elevation of FIG. 6;

FIG. 8 is a top elevation of the apparatus of FIG. 6;

FIG. 9 is an exploded view of the apparatus of FIG. 6;

FIG. 10 is an enlarged top elevation of the apparatus of FIG. 6 showing a ring in place upon the expanding apparatus;

FIG. 11 is a section on 11—11 of FIG. 10;

FIG. 12 is a partially sectioned partial view of the expanding apparatus showing a ring as expanded;

FIG. 13 is a view similar to FIG. 12, in reduced scale, and showing the effect of a change of the angle between the handles upon the expansion configuration of the ring.

DESCRIPTION OF A PREFERRED EMBODIMENT

A pig 10, having a customary tail 11, is shown in FIG. 1. FIG. 1 illustrates a human hand 21 holding the tail 11 with another human hand 22 operating an expanding device 30 which has expanded ring 100 through which the tail 11 has been inserted.

FIG. 3 illustrates the manner in which the ring is removed from the expanding device 30. The thumb 23 of the user of the device is merely moved forward and pushed against the ring 100 which literally then rolls off of the expanding pegs 36, 46 (and 66, not shown).

As is shown in the partial section FIG. 4, the ring 100 exerts a strong pressure at 101 completely around the circumferance of the tail 11. This pressure is such that all flow of blood is completely shut off from the tail 11. The skin, 12, of the stub of the tail is drawn in as indicated in FIG. 5, and essentially stretched until it comes together at 13. The tail 11 just drops off at the end of a few days of this constriction and deprivation of blood. The ring then, of course, also drops off, leaving a bloodless joinder of the skin at 13. This is particularly illustrated in FIG. 5.

FIGS. 6 and 9 should be viewed together for a complete understanding of the unique expanding device utilized in practicing the method of this invention. It will be seen that the tool comprises a pair of members 33 and 43, having holes 34 and 44, and extensions 35 and 45, respectively. Extensions 35 and 46 terminate in expanding pegs 36 and 46, respectively. Each of the members 31 and 41 has a plastic or other suitable handle covering 32 and 42, respectively.

The bushing member 51 comprises a head 52 with a round shoulder 53 having interior threaded portion 54. This bushing member is inserted through hole 56 in member 55 and then through hole 34, hole 44, and slot 56 in sliding member 65. The cap screw 61, having head 62, and threaded portion 64, which engages the threads 54, is utilized to maintain the entire tool in its assembled condition.

The spring 70 is connected by a loop 71 through hole 58 in tab 57 at one end and through loop 72 inserted into hole 68 in tap 67 at its other end. The tab 67 extends between the two bearing portions 33 and 43 of the members 31 and 41.

In its totally closed condition the tool is as shown in FIGS. 6, 7 and 8. The three ring holding prongs 36, 46 and 66 are shown together as they are when the tool is in its closed position. The ring 100 will be able to slip over or be rolled upon pegs 36, 46 and 56 when in the condition shown in FIG. 6.

FIGS. 10 and 11 illustrate the ring 100 in an enlarged scale in position upon the pegs 36, 46 and 66 when the tool 30 is in its closed position. It will be observed that the spring 70 pulling through its two ends 71 and 72, holds the sliding member 65 in position such that the three prong pegs 36, 46 and 56 are together when the tool is not being activated.

When the handles 32 and 42 are squeezed together, the sliding member 65 is pulled toward the handle by the two surfaces 33 and 43 acting as inclined planes against the tab 67. As the handles are squeezed, the pegs 36 and 46 separate, and at the same time peg 66 is drawn in the direction as shown in FIG. 12, making a triangular opening in ring 100.

The exact triangular formation formed within the ring 100 may be altered by altering the angular relationship of the surfaces 33 and 43 as shown particularly in FIG. 13, wherein the altered planes are shown as 33a and 43a. By doing this, the angular relationships within the ring 100 have been changed.

The exact materials which can be utilized to practice the method of this invention and to construct the performed apparatus for practicing the method may be altered according to requirements and availability of materials. For example, the parts of the tool itself may be made of various metals, certain plastics, and the like.

The ring itself may be formed preferably from latex, but also certain plastic materials and the like may be used.

While the embodiment of this invention shown and described is fully capable of achieving the objects and advantages desired, it is to be understood that such embodiment has been shown for purposes of illustration only and not for purposes of limitation.

We claim:

1. Apparatus for expanding an elastic ring comprising in combination: a first handle, a first peg attached to said first handle, a second handle, a second peg attached to said second handle, a slidable member, a third peg attached to said slidable member, pivot means pivotally connecting the said first and second handles together and slidably connecting said slidable member to said handles in such manner that said first, second and third pegs lie in close proximity to one another so as to be insertable within the hole within the elastic ring, said first and second handles being elongated members which terminate at corresponding ends in hand-gripping portions, and further means cooperative with said slidable member and said first and second handles such that when the hand-gripping portions of said handles are moved toward one another, said third peg is moved away from the said first and second pegs and said first and second pegs are simultaneously moved away from one another, said first and second pegs being attached to the ends of said handles opposite from the hand-gripping portions of said first and second handles, said first handle having a flattened portion lying in a region between its hand-gripping portion and said first peg, said second handle also having a flattened portion lying in a region between its hand-gripping portion and said second peg, the flattened portions of said first and second handles being provided with openings therethrough for receiving said pivot means, said slidable member having a flat elongated plate portion, said third peg being positioned at the end of said flat plate portion which lies closest to said first and second pegs, said third peg projecting normal from said flat plate portion; said flat plate portion having an elongated slot through which said pivot means passes and said further means comprising a tab formed on said slidable member at the end of said flat plate portion opposite from said third peg, said tab projecting in a direction normal to said flat plate portion and opposite to the direction in which said third peg projects; edges formed on said first and second handles and facing each other to engage said tab as the hand-gripping portions of said handles are pivoted toward one another to slide said slidable member in a preselected direction that moves said third peg away from said first and second pegs for expanding said ring, and a spring bias means connecting said tab to said pivot means to bias said slidable member in a direction opposite to said preselected direction.

* * * * *